(12) United States Patent
Rebuffat et al.

(10) Patent No.: US 8,449,563 B2
(45) Date of Patent: May 28, 2013

(54) FRAGMENTABLE DEVICE FOR THE ANASTOMOSIS OF HOLLOW ORGANS

(75) Inventors: Carlo Rebuffat, Carate Brianza (IT); Riccardo Rosati, Milan (IT); Dante David, Cologno Monzese (IT)

(73) Assignee: AB Medica S.p.A., Lainate Mi (IT)

( * ) Notice: Subject to any disclaimer, the term of this patent is extended or adjusted under 35 U.S.C. 154(b) by 1072 days.

(21) Appl. No.: 12/094,261

(22) PCT Filed: Nov. 21, 2005

(86) PCT No.: PCT/IT2005/000676
§ 371 (c)(1),
(2), (4) Date: Sep. 18, 2008

(87) PCT Pub. No.: WO2007/057933
PCT Pub. Date: May 24, 2007

(65) Prior Publication Data
US 2009/0076532 A1 Mar. 19, 2009

(51) Int. Cl.
*A61B 17/08* (2006.01)
(52) U.S. Cl.
USPC .......................................... 606/153; 606/154
(58) Field of Classification Search
USPC .......................................... 606/153, 151, 154
See application file for complete search history.

(56) References Cited

U.S. PATENT DOCUMENTS

| 4,598,712 A | 7/1986 | Rebuffat et al. |
| 4,966,602 A * | 10/1990 | Rebuffat et al. .............. 606/154 |
| 5,290,298 A | 3/1994 | Rebuffat et al. |
| 5,697,943 A | 12/1997 | Sauer et al. |

FOREIGN PATENT DOCUMENTS

| EP | 0 335 552 | 10/1989 |
| EP | 0 362 163 | 4/1990 |
| EP | 0 698 376 | 2/1996 |

OTHER PUBLICATIONS

PCT International Search Report for PCT/IT2005/000676 filed on Nov. 21, 2005 in the name of Carlo Rebuffat et al.
PCT Written Opinion for PCT/IT2005/000676 filed on Nov. 21, 2005 in the name of Carlo Rebuffat et al.
Applicant's Amendment and Response to PCT Written Opinion of PCT/IT2005/000676 filed on Nov. 21 2005 in the name of Carlo Rebuffat et al.
International Preliminary Report on Patentability for PCT/IT2005/000676 filed on Nov. 21, 2005 in the name of Carlo Rebuffat et al.

* cited by examiner

*Primary Examiner* — Gregory Anderson
(74) *Attorney, Agent, or Firm* — Steinfl & Bruno LLP

(57) ABSTRACT

Fragmentable compression device for the anastomosis of hollow organs consisting of a pot-shaped body composed of two elements (1, 2), inserted one into the other and consisting of a plurality of composable sectors (5, 6), a third ring-shaped or hollow cylinder-shaped element (3) intended to be inserted into said pot-shaped body to clamp the edges of the organs to be anastomized, and a fourth element (4) also ring-shaped or hollow cylinder-shaped which is pressure-inserted into element (3) to compress said edges. Also elements (3, 4) consist of a plurality of composable sectors (7, 8). The axial dimension of the device is notably short so that, when it is applied in the vicinity of the anal canal of the patient, tenesmus is considerably reduced.

10 Claims, 2 Drawing Sheets

FRAGMENTABLE DEVICE FOR THE ANASTOMOSIS OF HOLLOW ORGANS

CROSS REFERENCE TO RELATED APPLICATIONS

The present application is the US national stage of International Application PCT/IT2005/000676 filed on Nov. 21, 2005.

The prsent invention relates to an improved device with fragmentable Compression rings for the anastomosis of hollow organs of the human body, such as Parts of the digestive tract, the intestine or the ano-rectal cavity.

Compression devices with fragmentable rings are already known in surgery and are intended for carrying out the anastomosis of the above-mentioned organs by pressing their terminal edges between the rings such that they necrotize. The pressure of the pressed tissues in the anastomized area keeps tightly compact and stable the fragmentable rings, which come to fragmentation when the necrosis has occurred due to the consequent lack of pressure by the tissues thereon. The ring fragments are finally expelled through natural paths.

A device of this type is disclosed, for example, in U.S. Pat. No. 5,290,298 and comprises three cylindrical rings which can be inserted into each other; the two inner elements, i.e. those having shorter radius, are fragmentable sinche they are formed of a plurality of sectors. In the surgical use, the edges of hollow organs to be anastomized are pressed between the first and the second ring due to the pressure exerted thereon by the innermost ring, the third one, when the latter is inserted inside the second one so as to press the second ring against the first one.

Known fragmentable devices have various drawbacks among which generating a tenesmus feeling which can last until the excretion of the rings, if they are applied close to the anal canal, such as in the muco-prolapsectomy operation. The tenesmus can be assoicated with the axial dimension of known devices, which are provided with a rather voluminous portion for the clamping thereof, which is felt by the organism as an extraneous body to be excreted when it is applied in the ana canal.

Furthermore, their constructional features give rise to significant manufacturing problems as they require a complex and expensive molding process due to numerous undercut features and wide thin walls.

Hence, the purpose of the prsent invention is to provide an improved fragmentable device for the anatomosis of hollow organs free from the above-mentioned drawbacks. Such purpose is achieved with the fragmentable device according to the present invention whose characteristics are specified in claim 1. Further characteristics of such device are specified in the subsequent claims.

The main advantage of the fragmentable device according to the present invention is that, when it is applied in the proximity of the anal canal, the tenesmus is greatly reduced and actually in a surprising way. It is believed that this depends on the fact that the axial dimension of the device is notably shorter than that of the known fragmentable devices.

Another advantage provided by the device according to the present invention is that also its fragments have dimensions considerably shorter than those of known devices, so that the excretion of the fragments through natural paths is highly eased.

Still another advantage provided by the device according to the present invention is that its rounded shapes, even in the details, minimize the irritation causes of the tenesmus, and make atraumatic the use of the device in the proximity of the anal canal.

A further advantage provided by the device according to the present invention is that its manufacturing process is much easier and cheaper, with respect to the manufacturing processes of known devices. In fact, each element of the device according to the present invention is formed of several parts identical to each other and characterized by a lower structural complexity, which allows the separated manufacturing thereof in cheaper molding operations.

These and other advantages of the fragmentable device according to the present invention will be evident to those skilled in the art from the following detailed description of an embodiment thereof with reference to the annexed drawings wherein.

Figure 1:
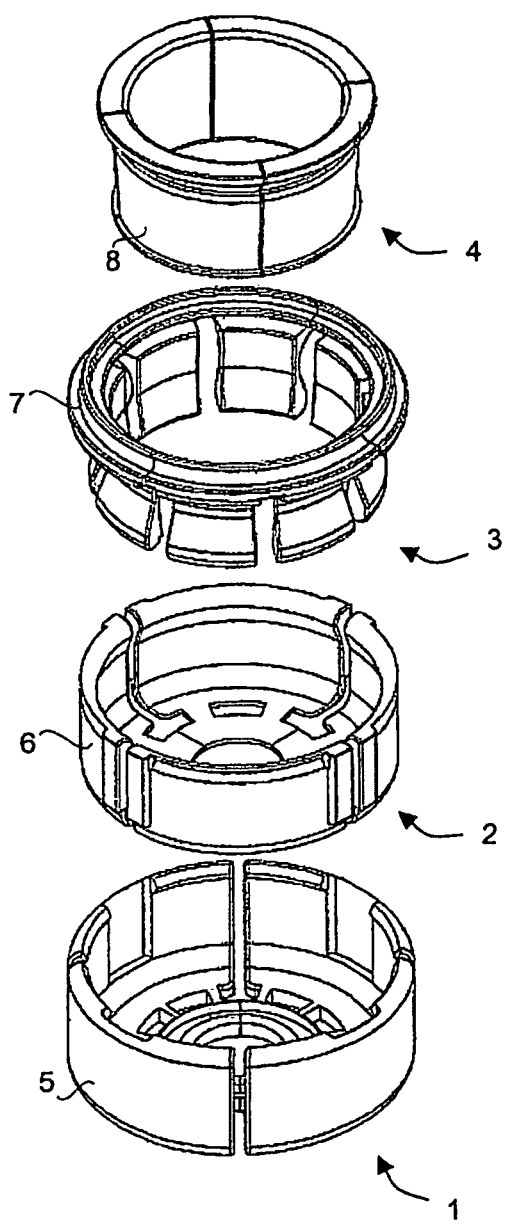
FIG. 1 shows a perspective exploded view of the fragmentable device.

In FIG. 1, there is seen that the improved device according to the present invention is composed of a first pot-shaped element 1, a second element 2, also pot-shaped and suitable to be inserted into the first element 1, a third element 3, shaped like a ring or a hollow cylinder suitable to be inserted into element 2, and a fourth element 4, also shaped like a ring or a hollow cylinder, suitable to be pressure-inserted into element 3.

As shown in the drawing, element 1 is formed in turn of a plurality of sectors identical to each other, which are four in the shown embodiment and are all designated with number 5. Element 2 is similarly formed of a plurality of sectors identical to each other which, in the illustrated embodiment, are also four and all designated with number 6. Also elements 3 and 4 are formed of four sectors identical to each other and which are respectively designated with numbers 7 and 8.

Before surgical use, element 2 is inserted into element 1 by means of a suitable tool so as to form a single pot-shaped body meant to receive the edges of the organs to be anastomized. During the surgery such edges are introduced in said pot-shaped body, already assembled, and then element 3 is inserted therein by means of the above-mentioned suitable tool, tightly keeping in place said edges. The edges interposed between elements 2 and 3 are then pressed by means of the pressure insertion of element 4 into element 3. In fact, due to the forced insertion of element 4 into element 3, the latter is radially dilated thus pressing the edges of the organs to be anastomized against the inner surface of element 2. Also the pressure insertion of element 4 into element 3 is carried out by means of the above-mentioned suitable tool. After inserting the elements into each other, a circular hole is made in the bottom of elements 1 and 2, thus putting the hollow organs in communication.

The device according to the present invention encloses and presses the edges of the hollow organs creating a constriction area such as to prevent the blood circulation to the involved tissues thus making them necrotize. When the necrosis has occurred, the pressure exerted on the device elements by said tissues ends and the device is fragmented into the individual sectors that compose the elements, and which are finally expelled through natural paths.

Figure 2:
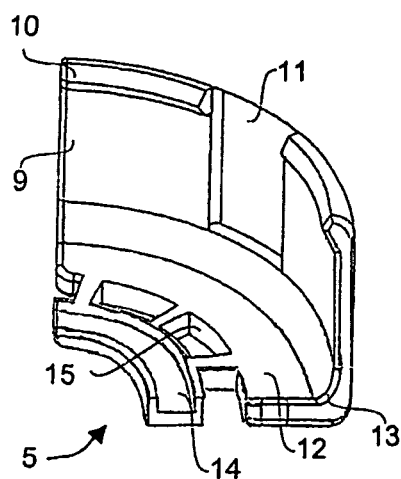
FIG. 2 shows a perspective view of one of the sectors of the first element.

With reference to FIG. 2, there is seen that each of the four sectors 5 forming element 1 is provided on the top of its mantle 9 with an arcuate edge 10 protruding inward and which is interrupted in the middle by a blind window 11. Mantle 9 is connected to the sector base 12 by an edge 13 suitably rounded on the outside and internally reinforced. The external rounded shape contributes to the reduction of tenesmus irritative causes and to making the use of the device atraumatic. The inner reinforcement grants a suitable stiffness in the use of the device, which makes it possible to react against the internal pressures exerted by the anastomized tissues.

In the base 12 of each sector 5 there is formed an arcuate groove 14 that is intended to receive a rib on the base of sector 6 as it will be described in the following with reference to FIG. 3. A series of through-openings 15 are arranged along an arc parallel to edge 13 and are intended to create in base 12 a structural weakening area suitable to be easily cut through by a suitable tool. The assembling of element 1 is directly made in the above-mentioned suitable tool by drawing the four sectors 5 close to each other and mating the side edges of the respective mantles 9 and the respective bases 12. In this way the pot-shaped body of FIG. 1 is obtained.

Figure 3:
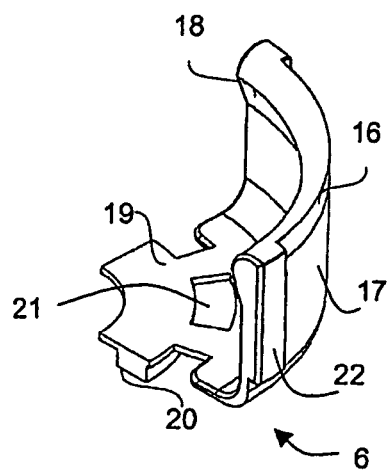
FIG. 3 shows a perspective view of one of the sectors of the second element.

In FIG. 3, there is seen that each of the four sectors 6 forming element 2 is provided with an arcuate groove 16 located on the external surface of their mantle 17 along the whole upper edge of the latter. This groove is sized so as to receive the arcuate edge 10 of mantle 9 of sector 5 described above. Mantle 17 of sector 6 is provided with a protrusion 18 on its internal surface along its upper edge. The base 19 of each of the four sectors 6 forming element 2 is provided with an arcuate, rib 20 and a series of through-openings 21 located along a circumferential arc. The through-openings arc intended to create a structural weakening area of base 19, in order to make it easy to cut therethrough by means of the above-mentioned suitable tool. Two vertical ribs 22 are provided along the side edges of mantle 17 of sector 6. Element 2 is assembled directly in the above-mentioned suitable tool by drawing the four sectors 6 close to each other so as to mate the side edges of their bases 19 and the vertical ribs 22 located along the side edges of the mantles 17, thus obtaining a pot-shaped body.

When element 2 is inserted in element 1, the protruding edges 10 of mantles 9 of each of the four sectors 5 of element 1 engage the grooves 16 of each of the four sectors 6 of element 2, and the vertical ribs 22 engage the blind windows 11. The arcuate ribs 20 of each of the four sectors 6 of element 2 fit into the arcuate grooves 14 of each of the four sectors 5 of element 1. In this way the two elements 1 and 2 result to be fixed one inside the other in the introducer tool, thus forming a single pot-shaped body as explained above. When assembling has been performed, the sets of through-openings 15 and 21 of the sectors 5 and 6 of elements 1 and 2 overlap, thus determining a single circular region of the base of the pot-shaped body suitably weakened to be cut by means of the suitable tool for connecting the anastomized organs. The geometric simplicity of sectors 5 and 6, owing to a lower number of undercut details and to less extended thin walls with respect to prior art devices, provides the above-mentioned advantages of easy manufacturing and low cost of the device according to the present invention.

Figure 4:
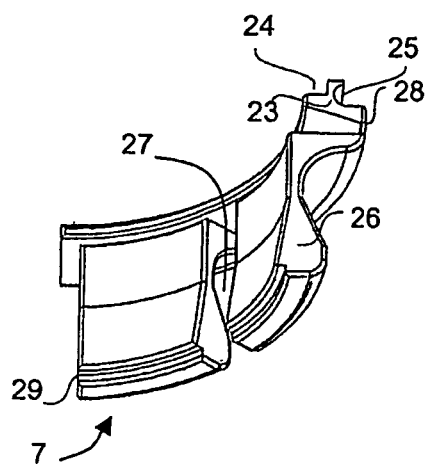
FIG. 4 shows a perspective view of one of the sectors of the third element.

In FIG. 4 there is seen that each of the four sectors 7 forming element 3, which is the one to be inserted in the pot-shaped element 2, consists of a base 23, which is a quarter of a circular ring, provided with an inward-facing groove 24 and an outward-facing groove 25 which allows the above-mentioned suitable tool to clamp sector 7. The base 23 is further provided with a plurality of tongues 26 spaced by slots 27. In the preferred embodiment there are two tongues 26. The sections 28 connecting tongues 26 to base 23 are such as to allow the bending of said tongues during the use of the device, as it will be described below. Each tongue 26 is characterized by a convex external surface and is further provided on the internal surface of its free end with an arcuate groove 29. Groove 29 and groove 24 of base 23 are made, for coupling sectors 7 of element 3 with sectors 8 of element 4, as it will be described later with reference to FIG. 5.

Element 3 is assembled by placing the four sectors 7 one adjacent to the other along a circumference directly in the above-mentioned tool where elements 1 and 2 are assembled. In the surgical use, element 3 is inserted by means of said tool into the pot-shaped element 2 thus enclosing the edges of the organs to be anastomized and tongues 26 move inwards to overstep the constriction area determined by the protrusions 18 of sectors 6 of element 2 thanks to the flexibility of their connecting section 28. Once said constriction area has been overstepped, tongues 26 tend to go back resiliently outwards to their initial position, thus compressing through their convex profile the edges of the organs clamped between element 2 and element 3.

Figure 5:
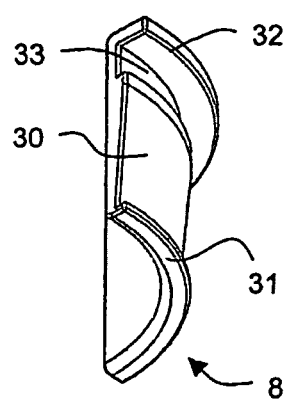
FIG. 5 shows a perspective view of one of the sectors of the fourth element.

In FIG. 5 there is seen that each of the four sectors 8 of element 4, which is the one to be pressure-inserted into element 3, consists of a mantle 30 which is provided with a bottom flap 31 and a top flap 32 suitable to engage respectively the arcuate grooves 29 and 24 formed in each of the four sectors 7 of element 3. Said flaps 31 and 32 have the further function of stiffening ribs for the sector, thus allowing to obtain a circumferentially stiff ring element 4, suitable to compress element 3 and the edges of the tissues to be anastomized without undergoing any deformation therefrom. Further, mantle 30 is provided with a groove 33 adjacent to the top flap 32 along the entire extension of the latter. Similarly to element 3, the four sectors 8, once they are placed one beside the other directly in the above-mentioned suitable tool, form element 4. When the latter is pressure-inserted in element 3 by means of the suitable tool, each bottom flap 31 of sectors 8 moves the corresponding tongues 26 of each sector 7 of element 3 radially outwards then snapping into the corresponding grooves 29 obtained at the free end of said tongues 26. Grooves 33 of sectors 8 of element 4 receive bases 23 of sectors 7 of element 3 and at the same time the top flaps 32 of sectors 8 abut against the arcuate grooves 24 of each sector 7 of element 3. In this way elements 3 and 4 are fixed one into the other and axially constrained by means of the above-described fits.

As already stated above, known devices for anastomosis may provoke a strong tenesmus in the patient, if applied in the vicinity of the anal canal, because of their dimensions. In the preferred embodiment of the present invention, the axial dimension of the device is remarkably reduced since the height of the part of the device to be clamped, consisting of base 23 of sector 7 of element 3 and its groove 25, has been decreased while maintaining unaltered the dimensions, of the surface compressing the edges of the organs to be anastomized. The total height of the above-illustrated embodiment of the device according to the present invention is not more than 11.6 mm.

Possible variations and/or additions may be made by those skilled in the art to the embodiment above described and illustrated in the annexed drawings while remaining within the scope of the invention. The same applies to the materials to be used for the manufacturing of the device or parts thereof. Any suitable material can be used, such as, for example, polyethylene terephthalate.

The invention claimed is:

1. A fragmentable compression device for the anastomosis of hollow organs comprising:
   i) a composable pot-shaped body composed of a first and a second element insertable one into the other,
   ii) a third ring-shaped or hollow cylinder-shaped element suitable to be inserted into said pot-shaped body, and
   iii) a fourth ring-shaped or hollow cylinder-shaped element suitable to be pressure-inserted into said third element, wherein:
   said first element is formed of a plurality of first individual separate sectors, each first individual separate sector being composable with another first individual separate sector by way of a first set of mating features located on each said first individual separate sector wherein said first set of mating features consists of smooth edges allowing juxtaposition of the first individual separate sectors so as to form said first element
   said second element is formed of a plurality of second individual separate sectors, each second individual separate sector being composable with another second individual separate sector by way of a second set of mating features located on each said second individual separate sector wherein said second set of mating features consists of smooth edges allowing juxtaposition of the second individual separate sectors so as to form said second element; and
   each said first individual separate sector being composable to each said second individual separate sector by way of a third set of mating features located on each said first individual separate sector and each said second individual separate sector wherein said third set of mating features includes:
   i) an internal surface of a bottom wall of each said first individual separate sector having an arcuate groove,
   an external surface of a bottom wall of each said second individual separate sector having an arcuate rib, said arcuate groove being suitable to receive said arcuate rib in an assembled configuration of the compression device;
   ii) each said first individual separate sector having a first mantle having a protruding arcuate edge formed at a top region of said first mantle,
   each said second individual separate sector having a second mantle having an arcuate groove formed at a top region of said second mantle, said arcuate groove being sized to receive said protruding arcuate edge in the assembled configuration of the compression device; and
   iii) said first mantle of each said first individual separate sector having a blind window at an intermediate portion of said first mantle,
   said second mantle of each said second individual separate sector having a vertical rib along a lateral edge of said second mantle, said blind window being suitable to receive said vertical rib.

2. The fragmentable compression device according to claim 1, wherein
   two or more sectors of said first element are identical to each other and
   two or more sectors of said second element are identical to each other.

3. The fragmentable compression device according to claim 2, wherein
   all the sectors of said first element are identical to each other and
   all the sectors of said second element are identical to each other.

4. The fragmentable compression device according to claim 2, wherein
   a bottom wall of each sector forming said first element is further provided with a series of through-openings and
   a bottom wall of each sector forming said second element is further provided with a series of through-openings, both said series of through-openings being arranged along an arc of circumference and suitable to overlap when the second element is inserted in the first element.

5. The fragmentable compression device according to claim 1, having a height lower than or equal to 11.6 mm.

6. The fragmentable compression device according to claim 1, wherein
   said second mantle has another vertical rib arranged along another lateral edge.

7. The fragmentable compression device according to claim 1, wherein smooth edges of the first set of mating features located on each said first individual separate sector comprises:
   the first mantle comprising side edges, and
   the bottom wall comprising side edges,
   wherein one first individual separate sector is composable with another first individual separate sector by way of mating side edges of respective mantles and mating side edges of respective bottom walls.

8. The fragmentable compression device according to claim 7, wherein each said first individual separate sector comprises edges suitable to connect the mantle with the bottom wall.

9. The fragmentable compression device according to claim 7, wherein smooth edges of the second set of mating features located on each said second individual separate sector comprises:
   the second mantle comprising vertical ribs, and
   the bottom wall,
   wherein one second individual separate sector is composable with another second individual separate sector by way of mating vertical ribs of respective mantles and mating side edges of respective bottom walls.

10. The fragmentable compression device according to claim 1, wherein smooth edges of the second set of mating features located on each said second individual separate sector comprises:
   the second mantle comprising vertical ribs, and
   the bottom wall comprising side edges,
   wherein one second individual separate sector is composable with another second individual separate sector by way of mating vertical ribs of respective mantles and mating side edges of respective bottom walls.

* * * * *

UNITED STATES PATENT AND TRADEMARK OFFICE
CERTIFICATE OF CORRECTION

PATENT NO. : 8,449,563 B2  Page 1 of 1
APPLICATION NO. : 12/094261
DATED : May 28, 2013
INVENTOR(S) : Rebuffat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1192 days.

Signed and Sealed this
Eighth Day of September, 2015

Michelle K. Lee
*Director of the United States Patent and Trademark Office*